United States Patent
Himley

(10) Patent No.: US 10,980,488 B2
(45) Date of Patent: Apr. 20, 2021

(54) DETERMINATION OF BLOOD PRESSURE MEASUREMENT CONFIDENCE USING VARIABLE MONITOR INACCURACY

(71) Applicant: PACIFIC DELTA LLC, Butte, MT (US)

(72) Inventor: Stephen Christopher Himley, Butte, MT (US)

(73) Assignee: PACIFIC DELTA LLC, Butte, MT (US)

( * ) Notice: Subject to any disclaimer, the term of this patent is extended or adjusted under 35 U.S.C. 154(b) by 45 days.

(21) Appl. No.: 16/137,198

(22) Filed: Sep. 20, 2018

(65) Prior Publication Data

US 2020/0093441 A1 Mar. 26, 2020

(51) Int. Cl.
*A61B 5/02* (2006.01)
*A61B 5/00* (2006.01)
*A61B 5/021* (2006.01)

(52) U.S. Cl.
CPC .......... *A61B 5/7221* (2013.01); *A61B 5/0004* (2013.01); *A61B 5/021* (2013.01); *A61B 5/743* (2013.01); *A61B 2560/028* (2013.01); *A61B 2560/029* (2013.01); *A61B 2560/0223* (2013.01); *A61B 2560/0242* (2013.01); *A61B 2560/0247* (2013.01); *A61B 2560/0252* (2013.01); *A61B 2560/0257* (2013.01); *A61B 2560/0266* (2013.01);
(Continued)

(58) Field of Classification Search
CPC ..... A61B 5/7221; A61B 5/0004; A61B 5/743; A61B 5/021; A61B 2560/028; A61B 2560/0257; A61B 2560/0252; A61B 2560/029; A61B 2560/0276; A61B 2560/0223; A61B 2560/0242; A61B 2560/0247; A61B 2560/0266; A61B 2562/0271; A61B 2562/029; A61B 2562/0219
See application file for complete search history.

(56) References Cited

U.S. PATENT DOCUMENTS 6,099,476 A * 8/2000 Engel ................. A61B 5/02208
600/490
6,241,679 B1 6/2001 Curran
(Continued)

OTHER PUBLICATIONS

International Search Report and Written Opinion for PCT/US2019/051296 dated Oct. 17, 2019; 12 pages.

*Primary Examiner* — Navin Natnithithadha
*Assistant Examiner* — Andrey Shostak
(74) *Attorney, Agent, or Firm* — Schwabe Williamson & Wyatt, PC

(57) ABSTRACT

Apparatuses and methods for displaying a blood pressure monitoring instrument reading along with inaccuracy values that vary over apparatus life and according to current operating conditions are disclosed. These inaccuracy values account for variability under different operating environments, over time and number of device measurement cycles, and across the range of possible instrument reading conditions. Determination of inaccuracy values may be based both on apparatus history and measurement under the current operating condition. Methods can further include informing a user of confidence in the instrument's current measurements based on the instrument's measurements and inaccuracy.

20 Claims, 7 Drawing Sheets

(52) U.S. Cl.
CPC . *A61B 2560/0276* (2013.01); *A61B 2562/029* (2013.01); *A61B 2562/0219* (2013.01); *A61B 2562/0271* (2013.01)

(56) References Cited

U.S. PATENT DOCUMENTS

| | | |
|---|---|---|
| 6,600,940 B1 | 7/2003 | Fein et al. |
| 7,018,335 B2 | 3/2006 | Kario et al. |
| 8,290,730 B2 | 10/2012 | Watson et al. |
| 8,715,194 B2 | 5/2014 | Cohn |
| 8,897,849 B2 | 11/2014 | Shirasaki et al. |
| 9,022,944 B2 | 5/2015 | Kawano et al. |
| 9,629,559 B2 | 4/2017 | Maarek |
| 9,936,920 B2 | 4/2018 | Muehlsteff |
| 2007/0060821 A1 | 3/2007 | Cohn |
| 2010/0268098 A1* | 10/2010 | Ito ............ A61B 5/022 600/490 |
| 2010/0286539 A1* | 11/2010 | Ito ............ A61B 5/022 600/499 |
| 2011/0071406 A1* | 3/2011 | Addison ......... A61B 5/0205 600/484 |
| 2013/0041270 A1 | 2/2013 | Chang |
| 2014/0066793 A1 | 3/2014 | Mukkamala et al. |
| 2014/0114153 A1* | 4/2014 | Bohm ............ A61B 5/495 600/345 |
| 2015/0073239 A1 | 3/2015 | Pei et al. |
| 2015/0182147 A1 | 7/2015 | Sato et al. |
| 2017/0360379 A1 | 12/2017 | Yang et al. |
| 2018/0020968 A1 | 1/2018 | Djajadiningrat et al. |
| 2018/0075207 A1 | 3/2018 | Schmidt |
| 2018/0360386 A1* | 12/2018 | LeBoeuf ............ A61B 5/742 |

\* cited by examiner

DETERMINATION OF BLOOD PRESSURE MEASUREMENT CONFIDENCE USING VARIABLE MONITOR INACCURACY

TECHNICAL FIELD

Disclosed embodiments relate to blood pressure monitoring accuracy; specifically, apparatuses and methods for providing confidence in assessment of blood pressure measurement are disclosed.

BACKGROUND OF THE INVENTION

The global prevalence of hypertension has been estimated at 1.39 billion adults in 2010 (Mills K. et al. Global Disparities of Hypertension Prevalence and Control: A Systematic Analysis of Population-based Studies from 90 Countries. Circulation. 2016 Aug. 9; 134(6): 441-450. doi: 10.1161/CIRCULATIONAHA.115.018912). It is responsible for at least 45% of deaths due to heart disease and 51% of deaths due to stroke (WHO. A global brief on Hypertension—Silent killer, global public health crisis. WHO/DCO/WHD/2013.2). The International Society for Hypertension (ISH) reports that only half of all people with hypertension are aware of their condition. This lack of awareness is especially severe in countries without high-income. Assessment for and diagnosis of hypertension occurs virtually entirely within clinical facilities, especially in countries without high income, i.e. lower resource settings (LRS). Hypertension is commonly detected using blood pressure measurements, such as provided by a blood pressure monitor. To determine whether a person has hypertension, to what degree, and an appropriate course of treatment, is facilitated by an accurate blood pressure measurement.

DETAILED DESCRIPTION OF THE INVENTION

Figure 1:
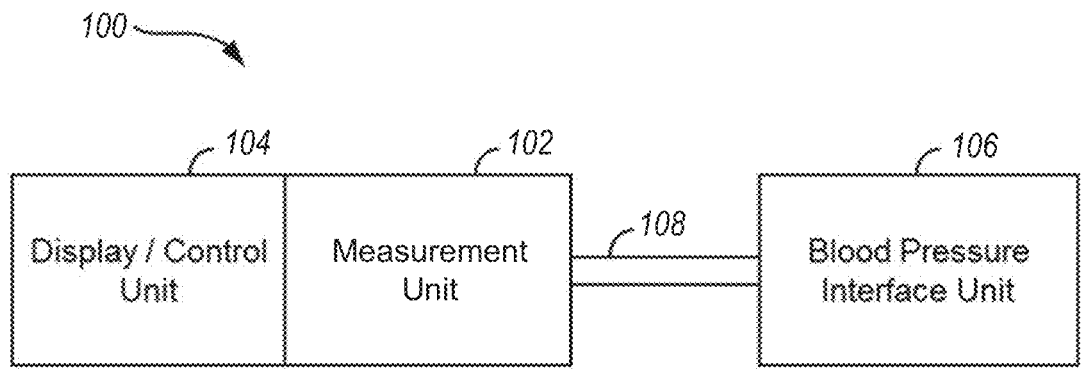
FIG. 1 is a diagram showing a blood pressure measuring apparatus configuration with the measurement unit integrated with a Display/Control Unit and attached to a blood pressure interface unit, according to various embodiments.

Digital blood pressure (BP) monitors may have inaccuracies in their measurements from day one of use, where a typical new unused device has a specified reading accuracy tolerance of up to +/−3 mmHg (millimeters mercury). Further, the inaccuracy of a new unused device may vary with pressure range, typically within 2% error at higher BP readings, e.g. a systolic BP reading of 200 mmHg could have an inaccuracy of up to +/−4 mmHg. Over time, as a device is used, the inaccuracies may grow. In a University of Ottawa study, 210 nephrology patients brought their home digital BP monitors to clinic where their readings were compared to clinical BP measurements using standard mercury sphygmomanometers (Ruzicka M. et al. How Accurate Are Home Blood Pressure Devices in Use? A Cross-Sectional Study. PLOS One, DOI:10.1371/journal-.pone.0155677 Jun. 1, 2016). Of these 210 digital BP monitors, 63 (30%) had systolic BP measurements that were 5 mmHg or more different from the standard, and 16 (8%) had systolic BP measurements that were 10 mmHg or more different from the standard.

Fitting these data to a normal (Gaussian) distribution of errors, these 210 digital BP monitors had a standard deviation of 5.2 mmHg. Thus, these users could have only a 44% confidence that their actual blood pressure was within the manufacturers' specified +/−3 mmHg of their digital BP monitor reading. This growth of inaccuracy of digital BP monitors over time must be accounted for when using BP measurements for clinical decision making.

A further complication of digital BP monitor readings occurs when they are used in non-ideal environments. BP monitors are qualified for use in climate-controlled room temperature and moderate humidity conditions. But in many global settings, BP measurements are made in much colder or much hotter environments, and across a wide range of humidity conditions. Knowing the inaccuracy of one's BP monitor in non-ideal settings is important when making diagnostic and treatment decisions.

The typical recommended re-calibration period for digital BP monitors is every 1-2 years. Measurement of blood pressure within clinical facilities is performed using blood pressure (BP) monitor devices, which can be re-calibrated at the recommended intervals with appropriate clinical engineering support. For many non-clinical or resource-limited settings (LRS), however, this translates into loss of confidence in device accuracy after only 1 to 2 years, due to the prohibitive costs or logistical burdens of re-calibration. Particularly in LRS, it may be cost-prohibitive to re-calibrate a digital BP monitor, which typically requires sending each unit back to the factory in another country for re-calibration. Re-purchase of new equipment every 1 to 2 years is also cost-prohibitive.

In high-income countries, while patients may continue to use their devices without re-calibration, the patients could keep a qualitative check of their home BP monitor readings by comparing them with the clinical readings during their periodic clinic checkups. When home BP monitor readings become far different from the clinic readings, this could signal replacement of their home BP monitors. However, the different settings of home and clinic produce naturally different BP readings, which makes this qualitative judgment difficult for patients to assess reliably.

After 1 to 2 years, the lack of confidence in accurate BP readings limits usage of home digital BP monitors to relative monitoring, which can be backed up with clinical support via frequent clinical checkups using calibrated BP monitors in clinical facilities. In LRS, where conditions are non-ideal and frequent checkups may not be possible, re-calibration is virtually non-existent. Medical equipment may be used as long as apparently functional, despite that home digital BP monitors used as primary clinical diagnostic instruments have large errors in their readings after only 1 or 2 years, with progressively larger errors over time. Clinical users of these devices may not know their BP monitors have become inaccurate, because the displays continue to show BP numbers without any indication of error, leading users to assume the readings are relatively accurate.

Diagnosis of hypertension requires repeat BP measurements, preferably over multiple days, and is best performed outside of clinic facilities to avoid masking and white-coat effects. In LRS, the costs of accessing clinic services even for one visit are prohibitive except for urgent or emergency conditions. Multiple visits for diagnostic purposes are cost-prohibitive. Thus, a device is needed where lay persons can perform repeat BP measurements at the community level, in client homes or nearby their homes.

A digital BP monitor used as a primary diagnostic instrument or used in home or community settings should incorporate information about its inaccuracy over the lifetime of the device, so the user knows how confident they can be in the displayed numbers. This inaccuracy must also account for the operating environment and the physiologic/acquisition conditions of the reading, i.e. larger error at higher blood pressure readings and low heart rate and high deflation rate for pneumatic type BP technologies. By including inaccuracy information over time to provide confidence in the readings, the useful life of a digital BP monitor in these settings could be extended from just 1 or 2 years to several years, with significantly decreased annualized equipment cost. This is particularly attractive in LRS where awareness of hypertension is very low and a very large number of people require screening and basic treatment. Extending the useful life of blood pressure monitors can enable community screening and identification of these people with hypertension and high cardiovascular risk.

Disclosed embodiments provide a method and an apparatus for reporting a blood pressure measuring instrument's readings to include the varying inaccuracy over the life of the instrument and according to current operating conditions, which informs the confidence in the instrument's current measurements. These inaccuracy values account for variability under different operating environments, over time and number of device measurement cycles, and across the range of possible instrument reading conditions. Determination of inaccuracy values may be based both on apparatus history and measurement under the current operating condition.

Blood pressure measurement readings may be reported along with inaccuracy values in various ways as described herein. These inaccuracy values account for the variability in inaccuracy under different operating environments, over time and number of device measurement cycles, and across the range of possible blood pressure reading conditions. This inaccuracy reporting is particularly important when such devices are used in settings over several years, in non-ideal conditions, and/or when they are not re-calibrated for whatever reason; the device includes instrument state-specific and operating condition-specific inaccuracy values in its readings.

The disclosed embodiments enable the confidence and reliable life of a non-invasive blood pressure measuring device to practically be extended from 1 or 2 years to several years, particularly in many operating conditions typically seen in lower resource setting countries. Such device life extension lowers the annualized cost, enabling their acquisition and long-term reliable use in lower resource settings.

In the following description, various aspects of the illustrative implementations will be described using terms commonly employed by those skilled in the art to convey the substance of their work to others skilled in the art. However, it will be apparent to those skilled in the art that embodiments of the present disclosure may be practiced with only some of the described aspects. For purposes of explanation, specific numbers, materials, and configurations are set forth in order to provide a thorough understanding of the illustrative implementations. However, it will be apparent to one skilled in the art that embodiments of the present disclosure may be practiced without the specific details. In other instances, well-known features are omitted or simplified in order not to obscure the illustrative implementations.

In the following detailed description, reference is made to the accompanying drawings that form a part hereof, wherein like numerals designate like parts throughout, and in which is shown by way of illustration embodiments in which the subject matter of the present disclosure may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

For the purposes of the present disclosure, the phrase "A or B" means (A), (B), or (A and B). For the purposes of the present disclosure, the phrase "A, B, or C" means (A), (B), (C), (A and B), (A and C), (B and C), or (A, B, and C).

The description may use perspective-based descriptions such as top/bottom, in/out, over/under, and the like. Such descriptions are merely used to facilitate the discussion and are not intended to restrict the application of embodiments described herein to any particular orientation.

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

It is the express intention that the claims are not to be construed in a means plus function form unless a claim being construed explicitly recites the words "means", "means to", or "means for." Absent the word "means", language such as "unit" or "module" is not to be construed as means plus function.

FIG. 1 shows an apparatus 100 according to a first possible embodiment in a configuration where a measurement unit 102 includes an integrated display/control unit 104. The measurement unit 102 is in turn in communication via communications link 108 with a blood pressure interface unit 106. The measurement unit 102 will be further described below. The blood pressure interface unit 106 could be any non-invasive blood pressure instrument technology, such as automatic inflating wrist cuff, brachial (arm) blood pressure measurement using auscultation or oscillometric technology, volume clamping technology, pulse transit time technology, or cuff-less finger pressure with photoplethysmography oscillometry technology, to name a few examples. Any technology now known or later developed for measuring blood pressure suitable for use with a measurement unit 102 as described herein may be employed.

Integrated display/control unit 104 can serve to provide various controls and monitoring for measurement unit 102. For example, display/control unit 104 may allow for triggering the start of a blood pressure measurement, where blood pressure interface unit 106 provides for an automated measurement cycle, e.g. an automatic inflating wrist cuff. In another example, display/control unit 104 may be used to signal the measurement unit 102 to begin recording or monitoring data from blood pressure interface unit 106, such as where blood pressure interface unit 106 is manually operated, e.g. a manual inflating/deflating cuff and bulb. Display/control unit 104 may further provide an interface for various functions and/or status of apparatus 100, such as performing diagnostic routines, displaying device usage history, environmental conditions, etc. Other functionality may include reconfiguring measurement unit 102 to accommodate a different style or type of blood pressure interface unit 106, where measurement unit 102 is configured to accept multiple types of blood pressure measurement equipment, and providing a user with instructional guidance for properly measuring blood pressure with the equipped blood pressure interface unit 106.

Display/control unit 104 may include an interface comprised of one or more displays to convey information to a user, as well as one or more ways by which the user may interact with display/control unit 104. Such interface may include a touch screen to provide both information to the user, as well as accepting input in the form of touches and/or gestures. Other examples may have a non-touch enabled screen or other type of display, e.g. LED, LCD, lamps, and similar indicators, along with one or more buttons, switches, sliders, etc., for accepting input. The particular configuration of display/control unit 104 for a given embodiment may depend upon the type of blood pressure interface unit 106 with which apparatus 100 is equipped. As described above, in apparatus 100 the display/control unit 104 is integrated and part of measurement unit 102, and so may share various components of measurement unit 102.

Figure 2:
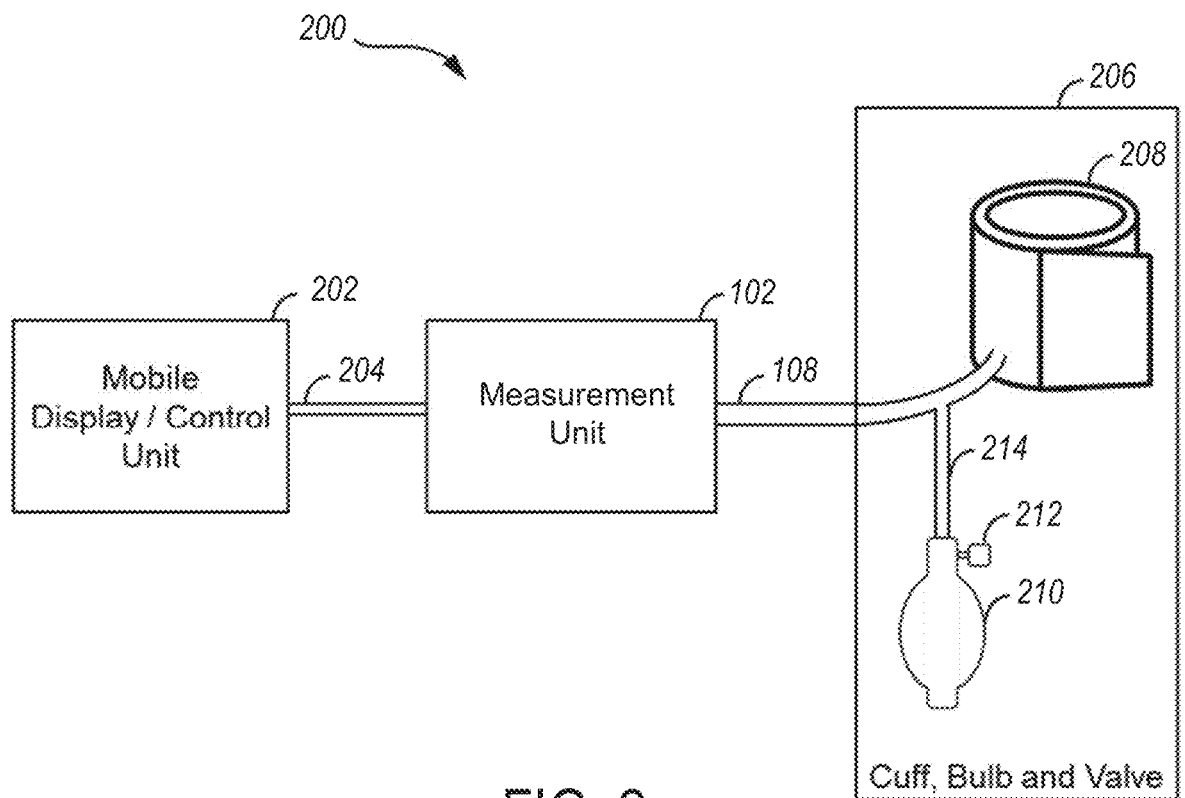
FIG. 2 is a diagram showing a blood pressure measuring apparatus in a mobile system configuration with the Display/Control Unit separate from the measurement unit that is attached to a blood pressure interface unit (shown as a brachial arm cuff and bulb in this example), according to various embodiments.

FIG. 2 shows an apparatus 200 according to a second possible embodiment equipped with a mobile display/control unit 202 that is external to and discrete from measurement unit 102, and connected to the measurement unit 102 by a communications link 204. Communications link 204 may be either wired or wireless, and may utilize any communications technology suitable to support communications between mobile display/control unit 202. Such technologies may include wireless technologies such as WIFI™, BLUETOOTH®, NFC™, ZIGBEE®, or other similar protocols. In one example, display/control unit 202 may be implemented as a dedicated interface unit, specific to measurement unit 102, and similar in implementation to display/control unit 104, save for being discrete from measurement unit 102. In another example, display/control unit 202 could be implemented in software, executable on a generic device such as a computer, mobile phone, laptop, tablet, wearable device such as a smart watch, or any other similarly suitable computing device now known or later developed.

Display/control unit 202 in apparatus 200 provides identical functionality to display/control unit 104 of apparatus 100. As used herein, "display/control unit 104" is intended to refer to embodiments either with the integrated display/control unit 104, or with the mobile display/control unit 202. As with the embodiment depicted in FIG. 1, display/control unit 202 can supply system power, display, and control of the data acquisition cycle performed by the measurement unit 102. Supply of power, control and display communication can be via a cable 204 or by wireless communication. In other embodiments, measurement unit 102 may have an independent power supply and/or control unit.

Blood pressure interface unit 206 may be implemented similar to blood pressure interface unit 106 of FIG. 1. The blood pressure measurement interface unit 206 in the example embodiment depicted in FIG. 2 is a brachial arm or wrist cuff and hand bulb. As shown, blood pressure interface unit 206 includes an inflating cuff 208, configured to go around a patient's arm or wrist. An inflation bulb 210 is pneumatically connected to inflating cuff 208 via air hose 214. A valve 212 is interposed on air hose 214 between inflation bulb 210 and inflating cuff 208 to control the inflation of inflating cuff 208. As will be understood by a person experienced in operating a blood pressure measurement cuff, when valve 212 is closed, air is forced from inflation bulb 210 into inflating cuff 208 when inflation bulb 210 is squeezed, thereby inflating the cuff. When valve 212 is opened, the air under pressure within inflating cuff 208 is released, causing inflating cuff 208 to deflate. The speed at which inflating cuff deflates may depend upon the extent to which valve 212 is opened. As depicted, blood pressure interface unit 206 may be operated manually. In such an embodiment, apparatus 200 may be configured to receive blood pressure measurements upon signalling by an operator, who would then proceed to inflate and deflate the inflating cuff 208 according to known procedures for measuring blood pressure.

In other embodiments, inflation bulb 210 and valve 212 may be automated to various extents, to allow automatic inflation and deflation of inflating cuff 208, such as where apparatus 200 is configured to automatically measure the blood pressure of a patient. For example, inflation bulb 210 may instead be implemented as a motorized air pump or compressor, with valve 212 being automatically actuated. In such embodiments, measurement unit 102 may control the automation of blood pressure interface unit 206 to effect automatic measurement of blood pressure. A display/control unit 104 may allow the operator to trigger the automatic cycle for measuring blood pressure.

Blood pressure interface unit 106 and 206 each may connect to measurement unit 102 via a communications link 108, which, in various embodiments, may be a cable, or via a wireless connection using any suitable communications technology. Such implementations may be used where measurement unit 102 receives the measurement numbers from blood pressure interface unit 106, which itself handles the actual measuring and quantifying of the physical signals (e.g. pressure changes, optical changes, etc.) from the blood pressure measurement. In other embodiments, such as where measurement unit 102 includes a module or functionality for performing the actual measuring and quantifying of blood pressure, communications link 108 may conduct physical signals, e.g. air pressure, hydraulic pressure, light, etc., as appropriate to the specific implementation of blood pressure interface unit 106/206. For example, in embodiments where measurement unit 102 includes a sensing unit necessary to acquire blood pressure measurements from the attached blood pressure interface unit (discussed below), communications link 108 may be implemented to carry physical signals to the sensing unit. In the embodiment depicted in FIG. 2, where blood pressure interface unit 206 includes an inflating cuff, communications link 108 is implemented as a pneumatic hose, with the sensing unit of measurement unit 102 configured to measure air pressure changes, the air pressure changes reflecting blood pressure. In still other embodiments, communications link 108 may carry both physical signals as well as communications, such as where measurement unit 102 includes a sensing unit, and blood pressure interface unit 106 is automated to allow for automatic capture of blood pressure measurements.

Figure 3:
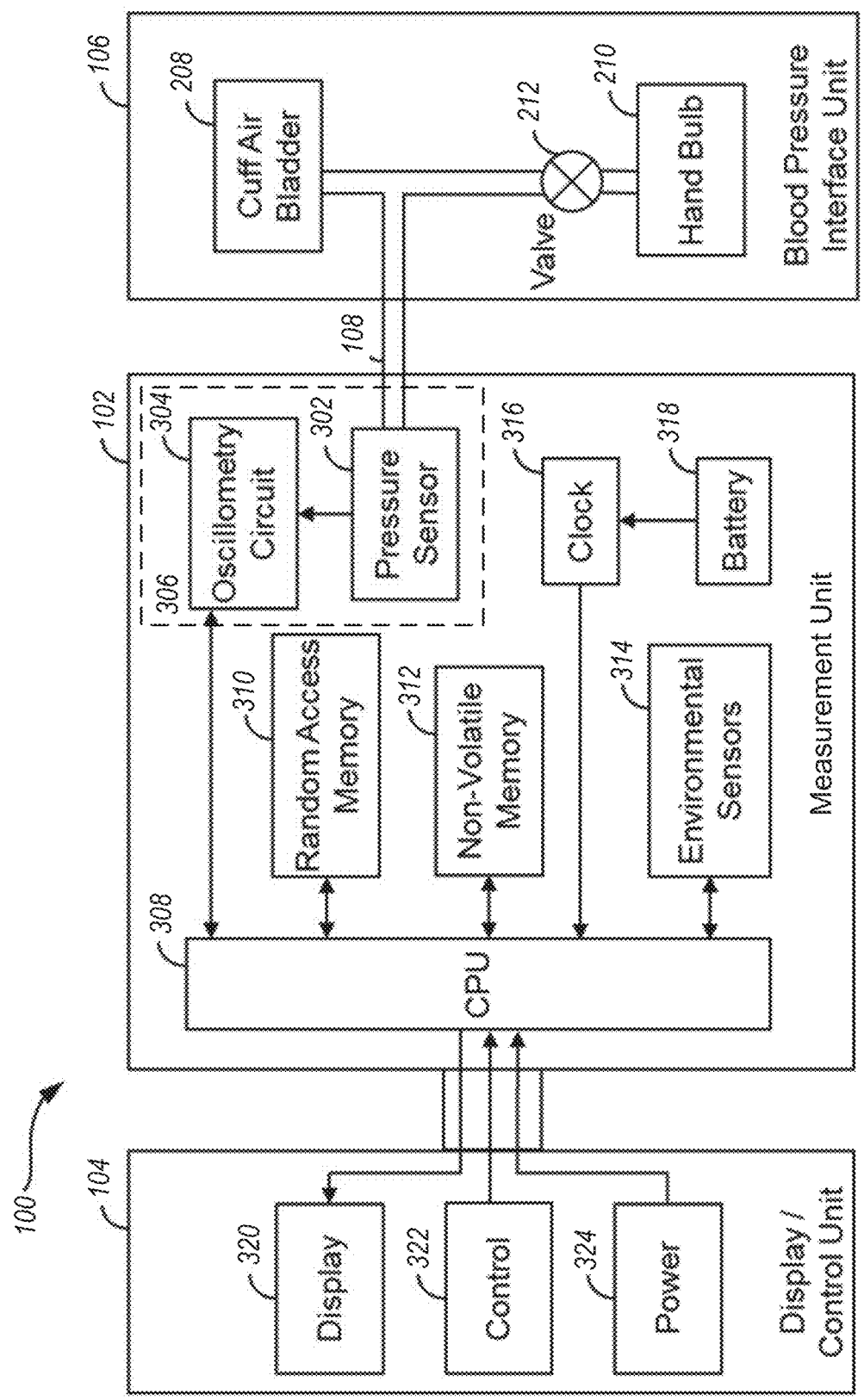
FIG. 3 is a diagram showing a possible architecture for a blood pressure measuring apparatus that maintains status of measurement unit inaccuracy, according to various embodiments.

FIG. 3 is a block diagram showing the architecture of a blood pressure monitoring apparatus according to various embodiments that monitors measurement unit 102 inaccuracy status and displays results accordingly. In the example depicted in FIG. 3, the blood pressure interface unit 106 includes an inflating cuff 208 and a hand-actuated inflation bulb 210 with valve 212, described above with respect to FIG. 2. Inflating cuff 208 contains an air bladder that is connected to a pressure sensor 302 within the measurement unit 102, which measures air pressure from communications link 108 continuously while an oscillometry circuit 304 determines at what points the air pressure reflects systolic blood pressure, mean blood pressure, and diastolic blood pressure, using simple or complex analysis in any state-of-the-art fashion to determine these points. The combination of pressure sensor 302 and oscillometry circuit 304 comprises a sensing unit 306, as described above with respect to FIGS. 1 and 2. Sensing unit 306 may, in other embodiments, be equipped with different modules that are appropriate to a particular implementation of blood pressure interface unit 106. In embodiments where blood pressure interface unit 106 includes integrated sensors and so delivers measurement numbers to measurement unit 102, sensing unit 306 may instead simply be a receiver for measurement data coming from blood pressure interface unit 106, via communications link 108.

In embodiments, measurement unit 102 contains a central processing unit (CPU) 308 that receives power from and communicates with the display/control unit 104. CPU 308 may be in communication with various types of storage, including volatile random access memory (RAM) 310 available for processing as well as non-volatile memory (NVM) 312 that does not lose information when power is disconnected. CPU 308 controls initiation of the sensing unit 306 and its data acquisition. CPU 308 further monitors and collects information from environmental sensors 314, which, in various embodiments, can include thermal, humidity, barometric pressure, and acceleration sensors. The choice of RAM 310 and NVM 312 may depend upon the selection of CPU 308, as well as any operating system or application-specific software that measuring unit 102 may use. NVM 312 may comprise, at least in part, firmware or other storage that contains any instructions or other software for operation of measuring unit 102. RAM 310 may be suitable for allowing CPU 308 to efficiently execute any firmware or software stored in NVM 312.

CPU 308 may be any suitable processor capable of carrying out and/or controlling or arbitrating the functions of sensing unit 306, and/or executing any firmware or software that may be stored in NVM 312. Examples of possible implementations of CPU 308 include general purpose processors, such as those available from ARM or Intel, an application-specific integrated circuit (ASIC), a field-programmable gate array (FPGA), discrete components, a combination of any of the foregoing, or another suitable implementation for performing the functions of measuring unit 102. It should further be understood that various components of measurement unit 102 may be integrated on to a single component, e.g. a System on a Chip (SoC) implementation as may be found in many ARM implementations and embedded controllers, such as those available from ATMel. SoC implementations may integrate one or more of RAM 310, NVM 312, CPU 308, clock 316, and environmental sensors 314 onto a single or a few components.

Environmental sensors 314 may include other sensors appropriate to a given implementation of measurement unit 102. Such sensors may include temperature, humidity, vibration/shock (such as with an accelerometer or gyroscope), particulates/atmospheric contamination, atmospheric pressure (such as with a barometer) and/or sensors for measuring any other environmental conditions that may affect the accuracy of apparatus 100. Such sensors may be implemented using any components now known or later developed.

A clock 316 and battery 318, preferably of a long-life type, can provide information on the age of the apparatus 100 since first operation. Clock 316, as used here, may be a real-time clock, as opposed to an oscillator for driving CPU 308. A real-time clock may allow tracking of total system age, as well as total system operational time, which may be used to help determine how age and operational time factors into device inaccuracy.

Various possible blocks in display/control unit 104 are also depicted in FIG. 3. As described above, display/control unit 104 may include a display 320 for providing operational status and/or instructions to a user. A control 322 may allow a user to manipulate various aspects of apparatus 100, such as triggering measurement of blood pressure, running diagnostics, viewing use history, environmental conditions, etc. As described above, control 322 may be integrated with display 320 in various embodiments, such as where display 320 is a touch screen (e.g. where display/control unit 104 is implemented as an app on a smartphone, with a touchscreen). In other embodiments, control 322 may be discrete from display 320. Display/control unit 104 may further include a power source 324, which may, in various embodiments, power not only the display/control unit 104 but also measuring unit 102 and/or blood pressure interface unit 106. In some embodiments, display/control unit 104 may be a smartphone, tablet, computer, or other similar device, running appropriate software and connected to measurement unit 102, such as by a wireless connection like BLUETOOTH®. Other embodiments may attach the device to measurement unit via a USB or other hard-wired interface, particularly where display/control unit 104 is to provide power to measurement unit 102 and/or blood pressure interface unit 106. Still further, display/control unit 104 may allow the user to enter client data (discussed below), and may inform the user via the display when apparatus 100 is ready for the user to inflate and then deflate the cuff (in the example depicted in FIGS. 2 and 3) in order to acquire a blood pressure reading.

In various embodiments, information stored in the NVM 312 may include inaccuracy characterization data determined for the specific model and/or lot number of measurement unit 102. Such inaccuracy characterization data may be calculated by the manufacturer of measurement unit 102 based on quality control and/or related testing of sample measurement units 102. The inaccuracy characterization data can provide a general curve of inaccuracy and/or degradation of measurement unit 102 that is inherent into a given design and production run of measurement unit 102. The inaccuracy characterization data may reflect degradation of measurement unit 102, current state of measurement unit 102 inaccuracy, and the categorization assessment algorithm discussed below. The inaccuracy characterization data may comprise the inaccuracy function described below, an equation or look-up table that is a function of time (age of the measurement unit 102), history of blood pressure measurement cycles, and the current environmental operating condition: temperature, humidity, barometric pressure, and vibration. Such data may be provided by clock 316 as well as environmental sensors 314.

With time and wear, measurement unit 102 inaccuracy may become progressively larger. In some embodiments, the current state of measurement unit 102 inaccuracy is updated using the inaccuracy function following each blood pressure measurement cycle, and the current inaccuracy may be stored in NVM 312. In other embodiments, measurement unit 102 inaccuracy may be computed on the fly with each test cycle on the basis of stored information in NVM 312, such as number of measurement/test cycles, environmental conditions experienced with each cycle, age of the measurement unit 102 determined from clock 316, and any other factors relevant or contributing to progressive inaccuracy of measurement unit 102. NVM 312 may further store information of previous calibrations, such as the last time the apparatus 100 was calibrated, the amount of correction required, the tolerance/inaccuracy of apparatus 100 following calibration, and other similar parameters or data points.

As discussed above, the accuracy of apparatus 100 (or 200) may decrease over time for a number of different factors. Measurement unit 102 can be configured to track, determine, and characterize the inaccuracy of a particular measurement at any time in the lifetime of the measurement unit 102. For some embodiments, it is not necessary to characterize each individual measurement unit 102, rather each model of measurement unit 102 for a given application. The inaccuracy of the measurement unit 102 may consist of contributions both dependent and independent of the current operating condition. The total inaccuracy of the measurement unit 102 for any given blood pressure reading at any given point in the life of the unit may be the combined contributions to inaccuracy of factors both dependent and independent of the current operating condition.

Some possible contributions to inaccuracy that are independent of current operating conditions include the aging of the internal components and the cycle history of these internal components. In embodiments, this history consists of the number of blood pressure measurement cycles experienced by the measurement unit 102. Since many sensors are composed at least partially of non-inert materials, these materials are subject to non-reversible physical changes when exposed over time to environmental factors such as temperature, humidity, pressure differences, and vibration. For many embodiments, temperature and humidity may have the greatest effect. These environmental factors can cause sensor response to change over time, thereby causing inaccuracy in readings compared to when measurement unit 102 was last calibrated. The cycle history may be modified by the particular environmental history seen by the measurement unit 102, with, for example, a larger inaccuracy value for units exposed to cycles at more severe temperatures and/or humidity levels than units exposed only at room temperature or to moderate humidity.

Another possible contribution to inaccuracy is, for implementations where blood pressure interface unit 206 is implemented as depicted in FIG. 2 and apparatus 200, a fluid overpressure event where the fluid sensor (e.g. pressure sensor 302/sensing unit 306) is exposed to very high pressure, such as an air pressure sensor used in oscillometry. The exposure to such events can be monitored and its contribution to inaccuracy included. Alternatively, physical means to protect the sensor against overpressure events can be included, for example, by incorporating a relief valve or other means to limit the pressure that the sensor experiences. It should be understood that apparatuses that implement blood pressure interface unit 106 using other technologies, e.g. light sensing, may have inaccuracies impacted by different conditions specific to the particular technology used in the given implementation.

Determination and characterization of the current inaccuracy of measurement unit 102, in one example, may include using the pressure sensor characteristic drift over time, typically in the range of 0.3 mmHg to 1.8 mmHg per year for high quality pressure sensors operating in the range of 0 to 300 mmHg. Other examples may include life-testing of the same make and model of measurement unit 102 under the various environmental conditions that affect accuracy of the unit. Typically, accelerated testing is conducted at extreme environmental conditions. The testing may result in creation of inaccuracy curves, an equation or look-up table that is a function of time (age of the measurement unit 102), and history of blood pressure measurement cycles at the environmental operating conditions of each cycle: temperature, humidity, barometric pressure, and vibration. Each model of measurement unit 102 requires testing, since different constellations of components produce different inaccuracy functions. More refined characterization could also be performed, such as characterization of measurement unit 102s for each lot of primary pressure sensor.

Any statistic and symmetric or asymmetric error distribution could be used for the inaccuracy value, but for illustration purposes, the inaccuracy value used herein is a standard deviation (SD) of a normal (Gaussian) distribution, with equal positive and negative errors of a reading. The SD and normal distribution allow determination of the probability of error at given confidence levels by calculating the area under the distribution curve. In other embodiments, the inaccuracy may be expressed as a tolerance range, such as depicted below with reference to FIG. 5A.

Figure 4A:
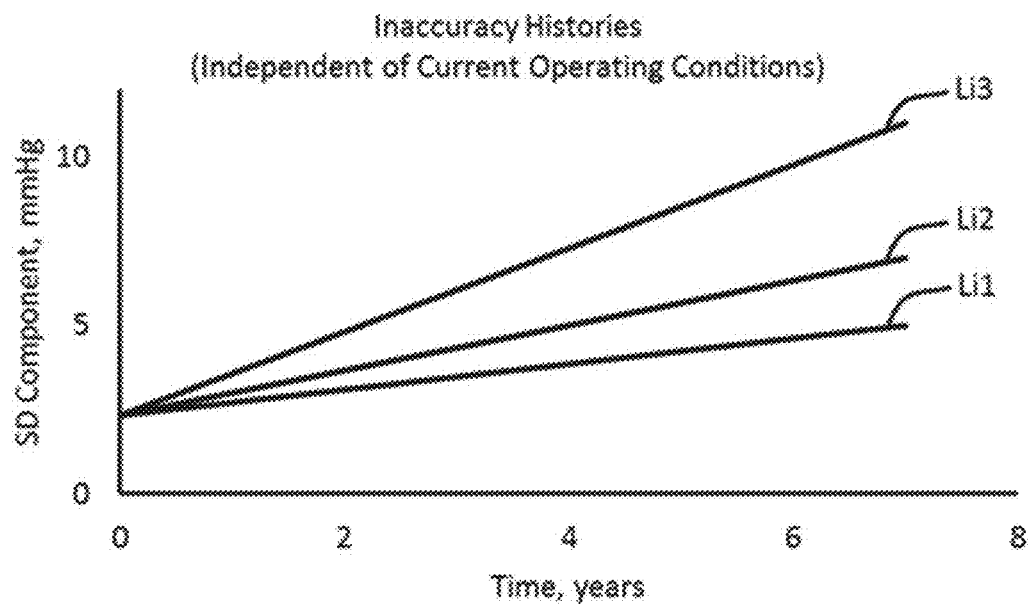
FIG. 4A shows example characteristic inaccuracy curves for measurement unit history, independent of current operating conditions.

FIG. 4A shows some example inaccuracy curves for measurement unit 102 histories, independent of current operating conditions. These curves are determined from characterization life-testing, with inaccuracy represented as the contribution to standard deviation error. Curve Li1 is representative of the contribution to standard deviation inaccuracy over time when the measurement unit 102 experiences a history of low number of measurement cycles per year with those cycles at room temperature and nominal relative humidity. Curve Li2 is representative of the growth in inaccuracy over time when the measurement unit 102 experiences a history of a low number of measurement cycles per year with those cycles at low temperature and nominal humidity. Curve Li3 is representative of the growth in inaccuracy over time when the measurement unit 102 experiences a history of high number of measurement cycles per year with those cycles at high temperature and high relative humidity. All these curves start out at the same point as new devices, in this example all at a standard deviation error of 2.3 mmHg.

Figure 4B:
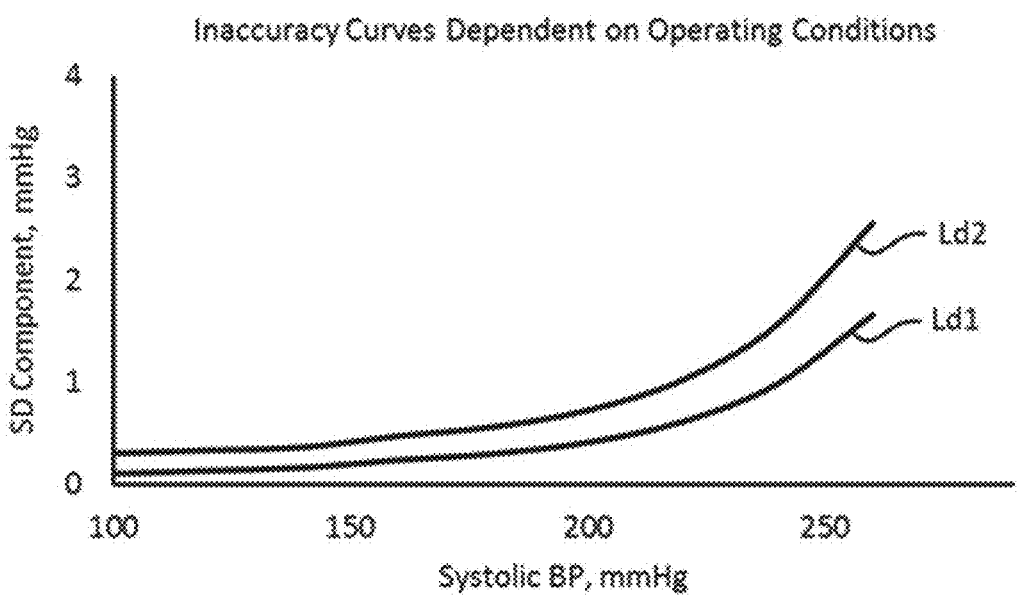
FIG. 4B shows example characteristic inaccuracy curves dependent on current operating conditions.

FIG. 4B shows example characteristic inaccuracy curves dependent on current operating conditions. Curve Ld1 shows the addition to standard deviation error when the heart rate is 100 beats per minute, nominal environmental conditions, and slow cuff deflation rate. Curve Ld2 shows the addition to standard deviation error when the heart rate is 60 beats per minute, nominal environmental conditions, and fast cuff deflation rate. The slower heart rate and faster cuff deflation rate of Curve Ld2 results in larger error contribution compared to Curve Ld1. As can be seen, the errors are larger at higher systolic blood pressure readings.

Contributions to inaccuracy that are dependent on current operating conditions may include the material response of sensors to current environmental factors such as temperature, humidity, pressure differences, and vibration. How a given sensor responds to such environmental factors may vary based upon the nature and type of sensor. These responses are typically reversible. For example, a systolic blood pressure reading at room temperature may be some nominal value for a given patient, but at high ambient temperature may be different for the same patient under the same physiologic condition. When the measurement unit 102 returns to room temperature the systolic blood pressure reading at room temperature returns to the same nominal value, assuming no hysteresis in the sensor over the given time span between readings at high and room temperature.

Other operating conditions that affect measurement unit 102 accuracy include the physiologic and acquisition conditions of the client's current blood pressure measurement. The measurement unit 102 may have a larger inaccuracy when the patient's systolic blood pressure is high, e.g. 200 mmHg, than when a patient's systolic blood pressure is normal, e.g. 120 mmHg. It may also have larger inaccuracy when the patient's heart rate is low and the pneumatic cuff deflation rate is high, leading to fewer data acquisition points. The operating condition-dependent inaccuracy of the measurement unit 102 is a combination of the contribution of the various environmental factors and the current physiologic/acquisition conditions of the blood pressure measurement. Further, different types of sensors may offer different degrees of inaccuracy variance for blood pressure ranges. For example, some types of sensors may offer a wider range of pressure sensing capabilities with little inaccuracy variance across the range, while other sensor types may vary widely.

As suggested above, how a particular type of sensor is used to capture a blood pressure measurement may impact its inaccuracy range. In at least implementations where blood pressure measurement is handled automatically (e.g. automatic cuff inflation and deflation), this inaccuracy may thus be controlled by tuning the control parameters/algorithms for the measurement automation. For non-automated or partially automated implementations, a user may be provided feedback during the measurement process, such as via display/control unit 104. For example, the user may be supplied guidance in proper operation of the blood pressure interface unit 106 to minimize inaccuracy. The guidance may be provided during the measurement process, such as a real-time indication of whether a particular operation is being conducted at an optimal pace, e.g. whether an inflating cuff is being deflated too slow, too fast, or at an ideal speed.

The current operating conditions may be obtained from sensors 314 internal to the measurement unit 102, for example a thermal sensor, a humidity sensor, a barometric sensor, and an accelerometer. Alternatively, the operator of the apparatus may input these operating conditions prior to initiating a blood pressure measurement. Some combination of user entry and internal sensing may also be used to determine current operating conditions.

In embodiments, the inaccuracy value for any given blood pressure reading is determined from an inaccuracy function which may use variables that can include the current measurement unit 102 age, current cycle history, current environmental operating conditions, and current physiologic/acquisition conditions of the blood pressure measurement. This inaccuracy function is a combination of the operating condition-independent inaccuracy curves, such as represented in FIG. 4A, and the operating condition-dependent inaccuracy curves, such as represented in FIG. 4B. In one embodiment, the total standard deviation (SD) inaccuracy for any given blood pressure reading is the sum of the current device SD based on its history plus the current device SD based on the current operating condition-dependent measurement. In other embodiments, the SDs from FIG. 4A and FIG. 4B may be weighted with respect to each other or, such as where current environmental conditions are determined to have an insignificant contribution to inaccuracy, may be omitted from the calculations altogether. Other possible ways of determining the total SD may be employed depending upon the nature of a given implementation of a blood pressure interface unit 106.

The inaccuracy SD described above may be computed on the fly, such as using a mathematical function, using a lookup table of precomputed values with environmental sensor readings and/or clock and date used as indexes into the lookup table, a combination of the foregoing, or any other suitable means of computation. In some embodiments, a lookup table may be stored into NVM 312 and/or RAM 310. Such a lookup table may be updated periodically on the basis of usage history of apparatus 100.

In embodiments, the computed inaccuracy value (expressed as a SD or otherwise) is incorporated into a current blood pressure reading. Various ways are possible to report the inaccuracy value, including but not limited to displaying high and low bounds, the nominal value +/− an error value, and graphical means with either color or grey scale information. A confidence value could also be reported, for example the systolic blood pressure reading and 90% confidence that the reading is within 3 mmHg error, or 95% confidence that the reading is within 5 mmHg error. Various statistical confidence levels could also be used, for example the +/− error could be one SD or 2 SDs or 3 SDs corresponding to 68% or 95% or 99.7% confidence respectively that the reading is within the error bounds.

Figure 5A:
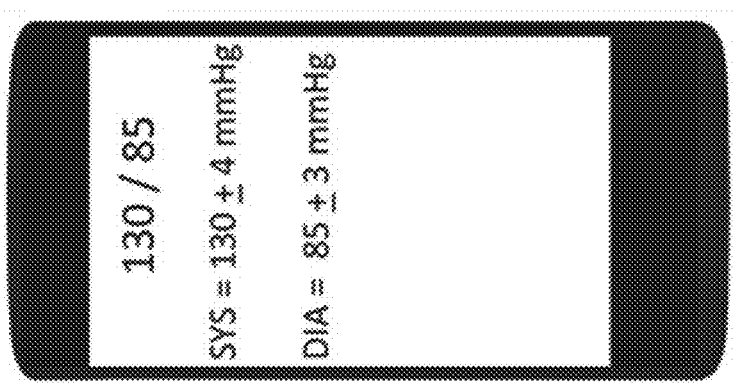
FIG. 5A shows an example way to display inaccuracy values using nominal values +/− error values, according to various embodiments.
Figure 5B:
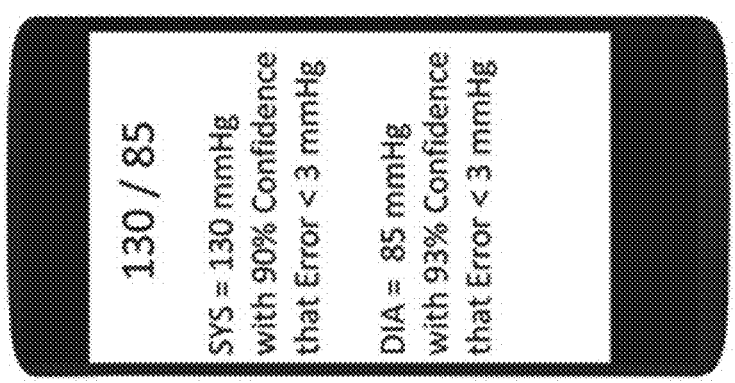
FIG. 5B shows an example way to display inaccuracy values using a confidence figure within error bounds, according to various embodiments.
Figure 5C:
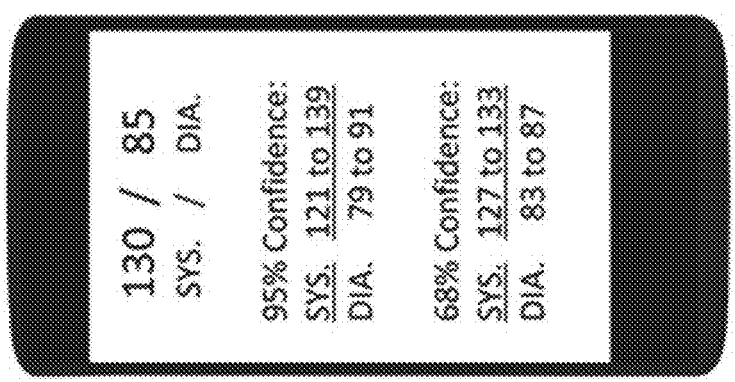
FIG. 5C shows an example way to display inaccuracy values as specific systolic and diastolic ranges for two confidence levels, according to various embodiments.
Figure 5D:
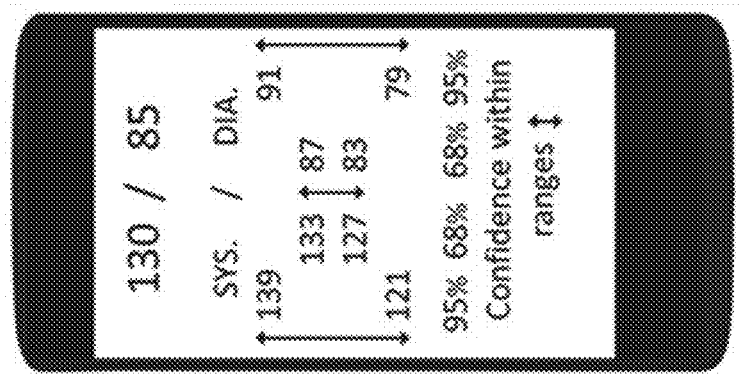
FIG. 5D shows an example way to display inaccuracy values using graphical ranges for two confidence levels, according to various embodiments.

FIGS. 5A-D show some example ways to display the foregoing inaccuracy values. FIG. 5A shows an example display of inaccuracy reporting using nominal values for systolic and diastolic blood pressure with +/− error values. FIG. 5B shows an example display of inaccuracy reporting using a confidence within fixed error bounds. FIG. 5C shows an example way to display inaccuracy values as specific systolic and diastolic ranges for two confidence levels. Note that a single inaccuracy value could be used for both systolic and diastolic blood pressure readings, based on, for example, mean blood pressure reading or systolic blood pressure reading. Alternatively, two separate inaccuracy values could be determined, an inaccuracy value for each systolic blood pressure reading and one for each diastolic blood pressure reading. FIG. 5D shows an example way to display inaccuracy values using graphical ranges for two confidence levels.

Figure 6C:
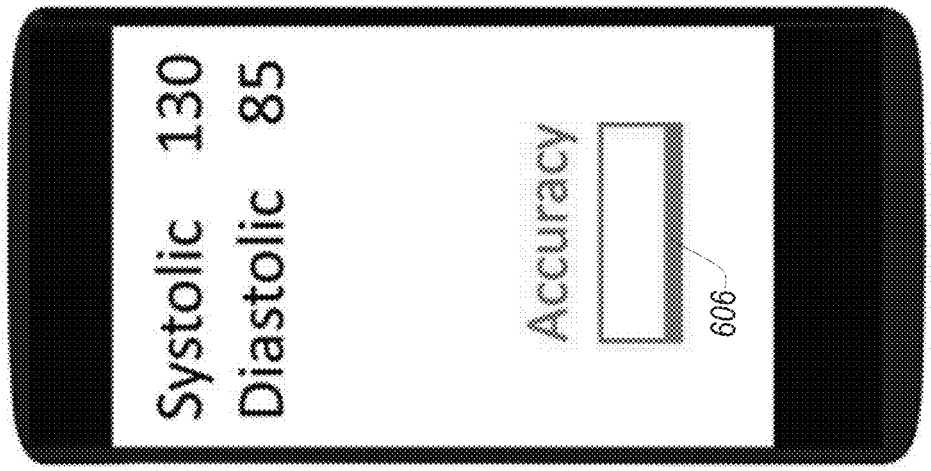
FIG. 6C shows an example graphical way to display inaccuracy, depicting a nearly empty box showing poor or low accuracy, according to various embodiments.
Figure 6B:
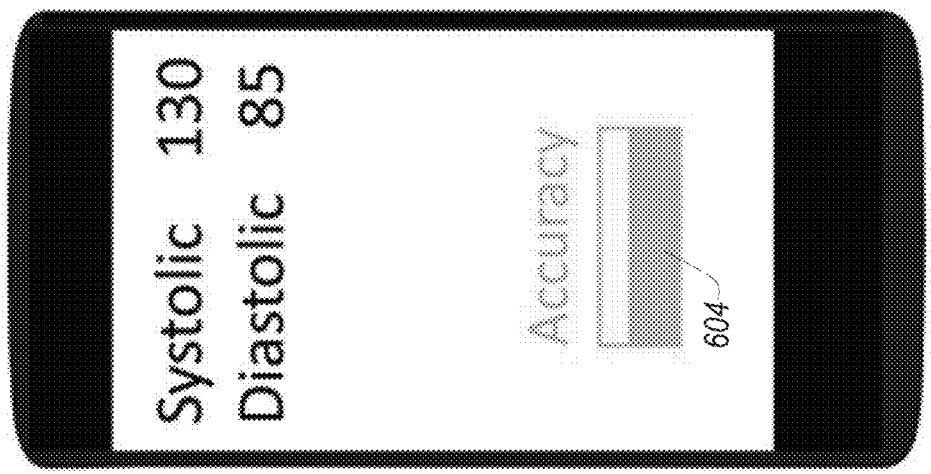
FIG. 6B shows an example graphical way to display inaccuracy, depicting a partially filled box showing moderate accuracy, according to various embodiments.
Figure 6A:
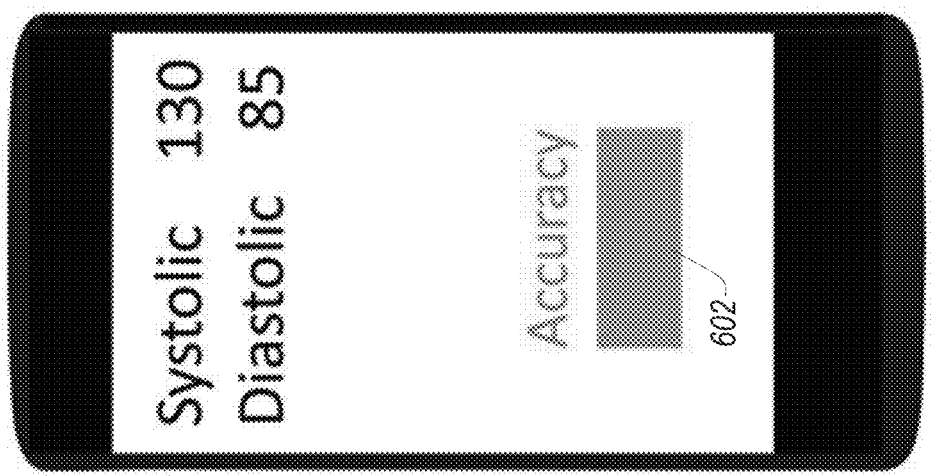
FIG. 6A shows an example graphical way to display inaccuracy, depicting a solid box indicating good or high accuracy, according to various embodiments.

FIGS. 6A-6C show an embodiment that employs a relatively simple means of relaying inaccuracy information to the user, presented using a fuel or battery gauge metaphor reflecting accuracy. FIG. 6A shows a display where inaccuracy is low/accuracy is high, indicated with a filled box 602, which could be colored green. FIG. 6B shows a display where inaccuracy is moderate, indicated with a partially filled box 604, which could be colored orange or yellow. FIG. 6C shows a display where inaccuracy is high/accuracy is low, indicated with a nearly empty box 606, which could be colored red. Warning messages could accompany these indicators, such as direction to recalibrate or service or replace the device. The box further could be configured to be continuously variably filled, rather than just a three-step depiction (full, mid, and empty), with the level of fill reflecting the actual inaccuracy range. Other embodiments may forego changing the fill of the box, and instead present a completely filled box, like box 602, with the color of the box changing to represent accuracy level, similar to a stop light. Still other embodiments may use a changing fill or pattern, rather than or in addition to color, to represent accuracy; such an embodiment may be useful for people who have deficient color vision that prevents them from easily distinguishing between red, orange, and green.

As the embodiments in FIGS. 6A-6C do not display the actual numerical range of inaccuracy (in contrast to FIGS. 5A-D), determining when to color change between high accuracy (green), moderate accuracy (orange/yellow), and low accuracy (red) may be done using at least two thresholds. If measured inaccuracy is within a first threshold for high accuracy/low inaccuracy, the display of FIG. 6A may be presented. If measured inaccuracy is within a second threshold but greater than the first threshold, the display of FIG. 6B may be presented. Finally, if the measured inaccuracy exceeds the second threshold for low accuracy/high inaccuracy, the display of FIG. 6C may be presented. In some embodiments, these thresholds may be employed in tandem with a variable fill of the accuracy box.

FIGS. 5A-D and 6A-C all depict a display that is part of a mobile device, such as a smartphone or tablet. As described above, such a mobile device may comprise a mobile display/control unit 202, and may receive such readings via a wired or wireless communications link 204 from measurement unit 102. In some embodiments, the display may be generated by the display/control unit 202 running appropriate software, with the relevant data supplied by measurement unit 102. In other embodiments, measurement unit 102 may generate the display, such as via HTML or XML, which is then rendered by a web browser on display/control unit 202. It should be understood that the mobile device representation presented in FIGS. 5A-D and 6A-C are only one possible implementation; a display/control unit 104, as described above, may present the information in a variety of other possible configurations, such as using discrete lamps and indicators, e.g. a combination of LED digits and lamps, alphanumeric LCD displays, or some combination of the foregoing.

In a further embodiment, the inaccuracy value is used in combination with one or more thresholds to support screening of clients for inclusion into or exclusion out of further action, for example clinical evaluation and potential treatment if measured systolic blood pressure is above a predetermined actionable threshold. In the current example, only a single threshold is used. However, the apparatus could present results for multiple thresholds. In this example, the apparatus measures systolic blood pressure, determines the current measurement unit 102 inaccuracy value, and then displays a confidence value for the client being above the actionable threshold. For example if the actionable threshold for the client is 160 mmHg, and the measurement unit 102 measures the client's systolic blood pressure as an estimated 170 mmHg with a current inaccuracy value being a standard deviation of 5 mmHg, then the apparatus would display that there is 95% confidence that the client is above the threshold, since the estimated systolic blood pressure is two SDs above the threshold. Alternatively the apparatus could display that there is only a 5% confidence that the client is below the threshold, or present both confidence values above and below the threshold.

Figure 7:
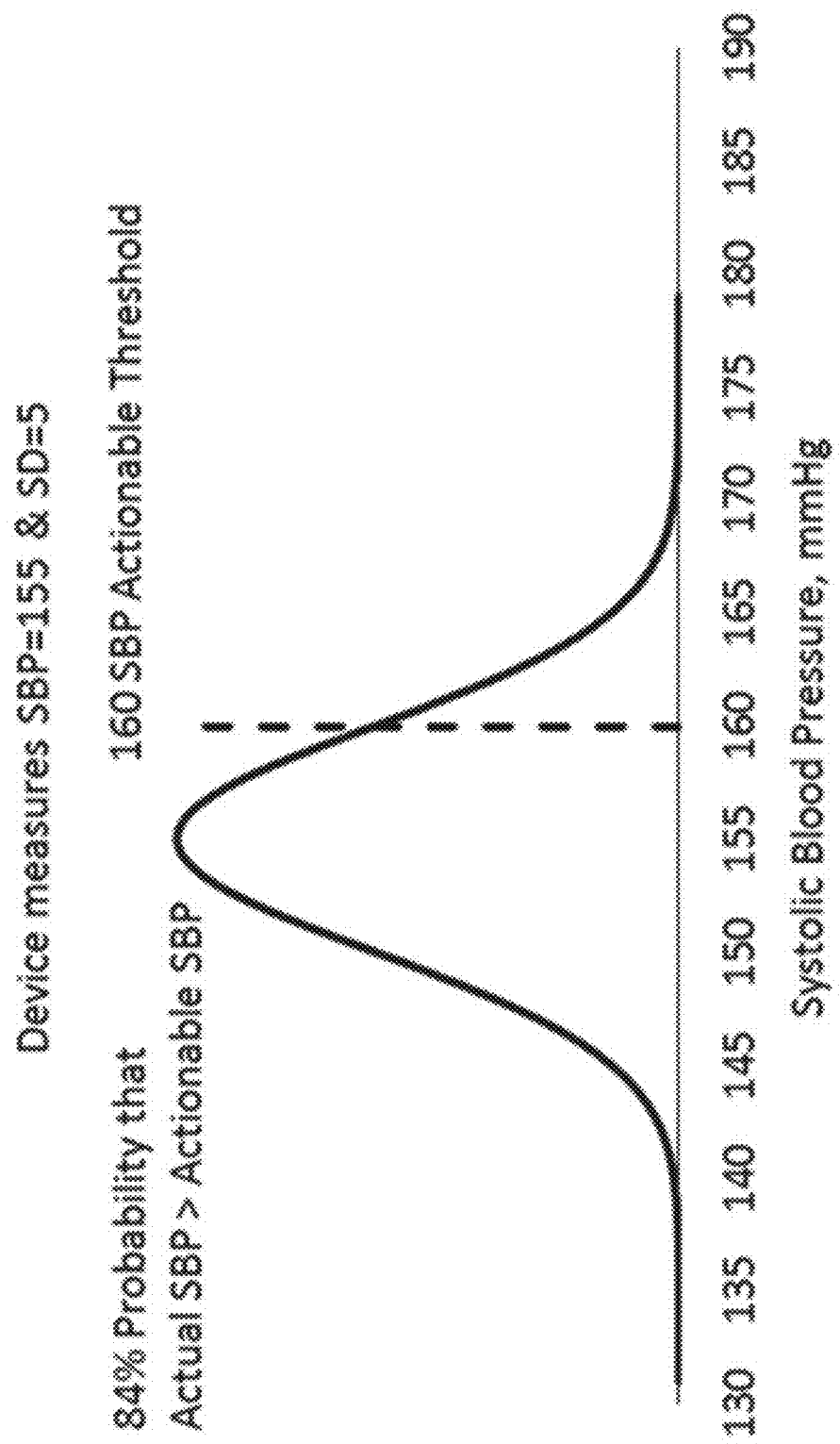
FIG. 7 shows a measurement example, where the probability of a measurement being below an actionable threshold is calculated, according to various embodiments.

FIG. 7 shows another measurement example where the actionable threshold is a systolic blood pressure of 160 mmHg, and the measurement unit 102 measures the client's systolic blood pressure as an estimated 155 mmHg with a current inaccuracy value being a standard deviation of 5 mmHg. In this case the apparatus would display that there is 84% confidence that the client is below the threshold. In FIG. 7, the curve is the normal distribution of likely actual systolic blood pressures for the apparatus reading of 155 mmHg, and the area under the curve to the left of the actionable threshold of 160 mmHg is 84% of the total area under the curve.

Screening can be performed at the community or village level with a mobile display/control unit 202 that has external communication ability, such as a smartphone. If a client has been identified as having a measurement higher than the threshold, the apparatus could prompt the user to send the current data to the receiving referral center, along with client identification information that the user would enter.

With availability of the inaccuracy value, a user of an apparatus 100 can be warned whenever the +/− error or SD exceeds some predetermined threshold, e.g. 10 mmHg. Such errors can occur at extreme operating conditions and high BP readings. As the apparatus ages and more cycles are experienced, such warnings would occur with more frequency, indicating to the user that the apparatus is approaching time for maintenance or re-calibration or replacement. The predetermined threshold may be selected for a point where apparatus 100 presents a level of inaccuracy that is unacceptably high for further clinical or diagnostic use. At such a point, the user may be advised to discontinue further use of the apparatus 100 until it can be serviced (in the case of inaccuracy due predominately to apparatus age) and/or environmental conditions improve (in the case of inaccuracy due predominately to extreme current environmental conditions) to bring its inaccuracy back down to an acceptable level.

The user can also be warned, prior to reaching a point where inaccuracy renders the apparatus 100 unusable, that the apparatus 100 should be maintained or re-calibrated or replaced at the point in apparatus life when the operating condition-independent inaccuracy value exceeds some second, possibly lower, predetermined threshold, e.g. 5 mmHg. This operating condition-independent inaccuracy value may be understood as the inaccuracy of the apparatus when operating under ideal room temperature and humidity conditions and for normal blood pressure readings. This value may increase with time and number of cycles, with the increase accelerated when operated under non-ideal conditions.

Where inaccuracy is due to apparatus usage and/or age, once apparatus 100 is serviced, NVM 312 may be reset with a refreshed table or curve for computing inaccuracy reflecting the new age and/or condition of any refurbished, serviced, or replaced components. Such a reset may be performed by the facility or person(s) performing the service.

Determination of the inaccuracy value could occur via processing within the measurement unit 102 itself or via processing within the associated display/control unit. Confidence level calculation could occur via processing within the measurement unit 102 itself or via processing within the associated display/control unit. If determination of the inaccuracy value occurs via processing within the measurement unit 102, multiple mobile display/control units 202 could be attached to the same measurement unit 102 at different times. This would enable different users to measure blood pressure by connecting the measurement unit 102 and blood pressure interface unit to their own mobile display/control units, for example their own smart phones.

Figure 8:
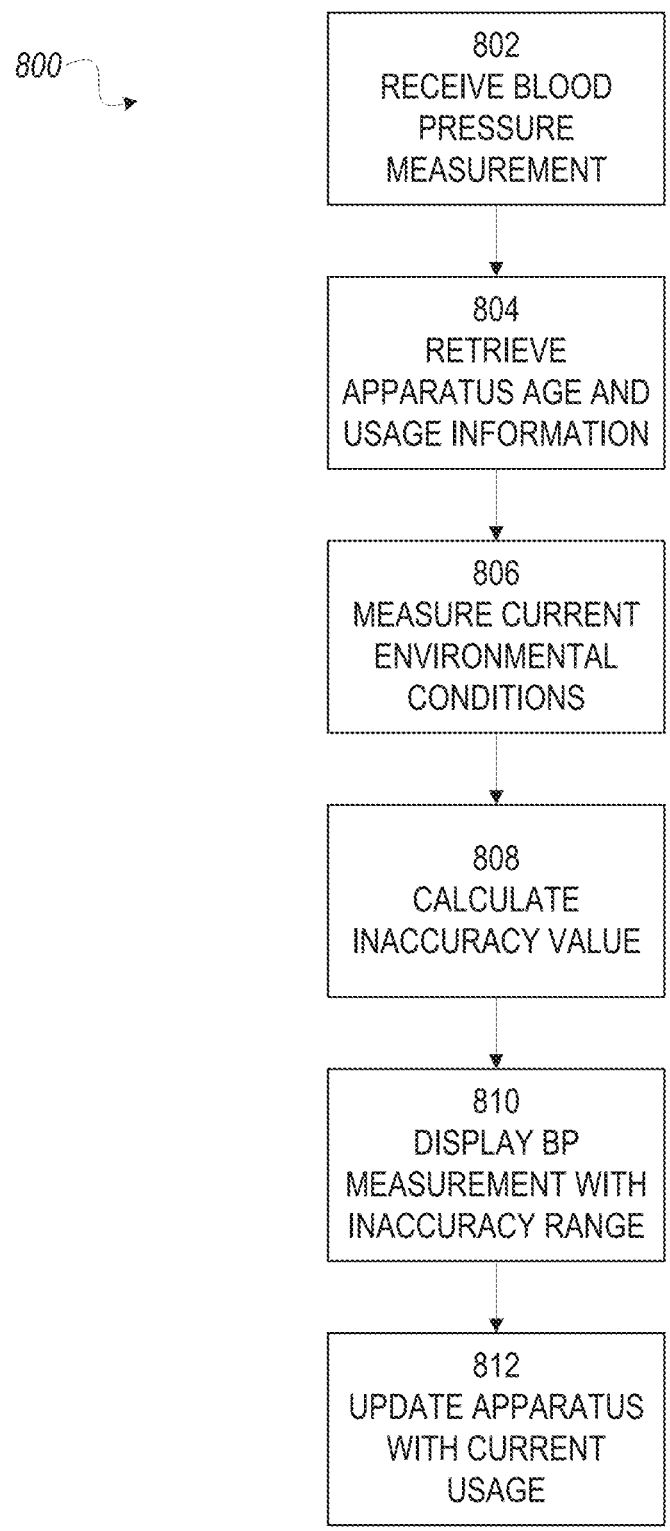
FIG. 8 depicts a flowchart of operations of a method for displaying measurement inaccuracy in blood pressure measurement, according to various embodiments.

FIG. 8 is a flowchart of a method 800 that may be performed in whole or in part by an apparatus 100 (or 200), for calculating the inaccuracy of a blood pressure measurement. The various operations of method 800 should be understood with respect to the foregoing disclosure, and may be carried out by the same or different portions of apparatus 100. For example, operations may be carried out by measurement unit 102, by display/control unit 104/202, by an external device such as a mobile device (regardless of whether configured to act as a display/control unit 202), or a combination of any of the foregoing. Method 800 may be implemented in hardware, such as using dedicated or purpose-specific components, in software, such as using instructions executable by measurement unit 102 (specifically, CPU 308) and/or display/control unit 104, the instructions stored on a computer-readable medium (CRM), or a combination of the foregoing. Where implemented at least partially using a CRM, the CRM may be stored in NVM 312, RAM 310, or on another storage in measurement unit 102 and/or display/control unit 104.

In operation 802, the blood pressure of a patient is measured by the apparatus 100. The particular technique of obtaining the measurement will depend upon the particular implementation of a given apparatus blood pressure interface unit 106, as described above, and may be automated, partially automated, or performed manually.

In operation 804, the age of the apparatus and its usage (e.g. number of cycles and relevant conditions of each cycle) are obtained, such as from NVM 312 and clock 316. In operation 806, current environmental conditions may be obtained from environmental sensors 314.

In operation 808, the age of the apparatus, its usage, and/or environmental conditions (including external factors as well as patient-specific factors, such as inordinately high measurements) may be combined as described above and used to determine an inaccuracy value or range for the measured blood pressure from operation 802. As discussed above, the inaccuracy value may be obtained using a lookup table or mathematical function, in various embodiments.

In operation 810, the blood pressure measurement along with its inaccuracy range are displayed via display/control unit 104 or 202. As discussed above, the inaccuracy range may be displayed graphically, numerically, or in another suitably understandable fashion. In addition, in operation 810 a warning may be presented to the user of apparatus 100/200 if the inaccuracy range exceeds a first predetermined threshold, such as for a range that indicates that device servicing is recommended, and/or a second predetermined threshold, such as a range that indicates further usage of the device should be discontinued until servicing and/or until environmental conditions improve.

Finally, in operation 812, the apparatus 100, such as NVM 312, may be updated to reflect the usage of the most recent blood pressure measurement, e.g. the cycle count of the apparatus 100 is incremented. Additionally and as mentioned above, the particular cycle may include information about relevant environmental conditions, such as if the measurement was on an inordinately high pressure or environmental conditions that may result in accelerated degradation or otherwise adversely affect future readings. As discussed above, the specifics of what data needs to be updated and to what extent may depend upon the particulars of a given embodiment of apparatus 100/200.

Note that the embodiments disclosed above are understood to be in all ways exemplary and in no way limiting. The scope of one or more embodiments of the claimed invention is defined not by the aforementioned descriptions but by the appended claims. While the claimed invention has been described in detail with reference to specific embodiments, it is clear to those of ordinary skill in the art that many variations and modifications can be made without departing from the essence and scope of the claimed invention.

What is claimed is:

1. A method, comprising:
   receiving a blood pressure measurement value using a measurement unit;
   retrieving, from a storage equipped to the measurement unit, inaccuracy characterization data of the measurement unit, the inaccuracy characterization data comprising a general curve of degradation of the measurement unit and a current state of inaccuracy of the measurement unit;
   determining, with a processor equipped to the measurement unit and based at least in part upon inaccuracy characterization data of the measurement unit, an inaccuracy range of the blood pressure measurement value, the inaccuracy range at least partially reflecting measurement unit inaccuracies;
   displaying the blood pressure measurement value and the inaccuracy range; and
   updating the inaccuracy characterization data in the storage to include conditions of the measurement unit at the time of the blood pressure measurement value that affect measurement unit accuracy, including an age of the measurement unit, a number of cycles experienced by the measurement unit, and the environmental conditions in which the measurement unit is used.

2. The method of claim 1, wherein the inaccuracy characterization data includes one or more of an age of a blood pressure interface unit and physical conditions of measurement including acquisition rate and relative location of the blood pressure measurement value with respect to a measurement range of the measurement unit.

3. The method of claim 2, further comprising measuring environmental conditions with one or more of a temperature sensor, a humidity sensor, a barometric sensor, and an accelerometer in the measurement unit.

4. The method of claim 1, further comprising displaying a prompt to maintain or re-calibrate or replace the measurement unit when the inaccuracy range exceeds a predetermined threshold.

5. The method of claim 1, further comprising displaying a probability or confidence level that the blood pressure measurement value is above or below one or more predetermined thresholds.

6. An apparatus, comprising:
- a non-volatile storage;
- a processor;
- a blood pressure interface; and
- a measurement unit coupled to the blood pressure interface, to obtain a measured blood pressure from the blood pressure interface;
- wherein the measurement unit is adapted to:
  - retrieve, from the non-volatile storage, inaccuracy characterization data of the measurement unit, the inaccuracy characterization data comprising a general curve of degradation of the measurement unit and a current state of inaccuracy of the measurement unit,
  - determine, by the processor and based at least in part upon an inaccuracy characterization data, an inaccuracy range for the measured blood pressure, the inaccuracy range at least partially reflecting measurement unit inaccuracies,
  - update the inaccuracy characterization data in the non-volatile storage with each blood pressure measurement and environmental conditions that affect measurement unit accuracy, including an age of the measurement unit, a number of cycles experienced by the measurement unit, and the environmental conditions in which the measurement unit is used, and
  - cause the measured blood pressure and determined inaccuracy range to be displayed on a display and control unit.

7. The apparatus of claim 6, wherein the inaccuracy range is further determined based upon one or more of an age of the apparatus, and physiologic and acquisition conditions of a blood pressure measurement.

8. The apparatus of claim 7, further comprising one or more of a thermal sensor, a humidity sensor, a barometric sensor, and an accelerometer, coupled to the measurement unit.

9. The apparatus of claim 6, wherein the measurement unit is further adapted to cause a probability or confidence level that the measured blood pressure is above or below one or more predetermined thresholds to be displayed on the display and control unit.

10. The apparatus of claim 6, wherein the measurement unit is further adapted to cause a prompt to be displayed on the display and control unit to maintain or re-calibrate or replace the apparatus when the inaccuracy range exceeds a predetermined threshold.

11. The apparatus of claim 6, wherein the display and control unit comprises a mobile device coupled to the measurement unit via a direct cable or by a wireless link.

12. The apparatus of claim 6, wherein the display and control unit is integrated with the measurement unit.

13. The apparatus of claim 12, wherein the display and control unit is adapted to cause the measurement unit to automatically measure the blood pressure with the blood pressure interface.

14. The apparatus of claim 12, wherein the display and control unit is adapted to provide power to the measurement unit and blood pressure interface.

15. A non-transitory computer-readable medium (CRM) comprising instructions that, when executed by a processor on a measurement unit, cause the measurement unit to:
- receive a blood pressure measurement from a blood pressure interface unit;
- retrieve inaccuracy characterization data for the measurement unit from a storage, the inaccuracy characterization data comprising a general curve of degradation of the measurement unit and a current state of inaccuracy of the measurement unit;
- determine an estimated inaccuracy range of the measurement at least in part from the inaccuracy characterization data, the inaccuracy range at least partially reflecting measurement unit inaccuracies;
- display the blood pressure measurement with the estimated inaccuracy range; and
- update the inaccuracy characterization data in the storage to include conditions of the blood pressure measurement that affect measurement unit accuracy, including an age of the measurement unit, a number of cycles experienced by the measurement unit, and the environmental conditions in which the measurement unit is used.

16. The CRM of claim 15, wherein the instructions, when executed, cause the measurement unit to further determine the estimated inaccuracy range of the measurement based on one or more of physical conditions of measurement including acquisition rate and relative location of the blood pressure measurement with respect to a measurement range of the measurement unit.

17. The CRM of claim 15, wherein the inaccuracy characterization data comprises one or more of an age of the blood pressure interface unit, and a number of cycles experienced by the blood pressure interface unit.

18. The CRM of claim 15, wherein the instructions, when executed, further cause the measurement unit to further measure environmental conditions with one or more of a temperature sensor, a humidity sensor, a barometric sensor, and an accelerometer.

19. The CRM of claim 15, wherein the instructions, when executed, further cause the display of a prompt to maintain or re-calibrate or replace the measurement unit when the inaccuracy range exceeds a predetermined threshold.

20. The CRM of claim 15, wherein the instructions, when executed, further cause the display of a probability or confidence level that the blood pressure measurement is above or below one or more predetermined thresholds.

* * * * *